(12) United States Patent
Seilz et al.

(10) Patent No.: US 8,658,788 B2
(45) Date of Patent: *Feb. 25, 2014

(54) PROCESS FOR THE PRODUCTION OF 3-OXO-PREGN-4-ENE-21,17-CARBO-LACTONES BY THE METAL-FREE OXIDATION OF 17-(3-HYDROXYPROPYL)-3,17-DIHYDROXYANDROSTANES

(75) Inventors: Carsten Seilz, Boenen (DE); Hartmut Seba, Unna (DE)

(73) Assignee: Bayer Pharma AG, Berlin (DE)

( * ) Notice: Subject to any disclaimer, the term of this patent is extended or adjusted under 35 U.S.C. 154(b) by 32 days.

This patent is subject to a terminal disclaimer.

(21) Appl. No.: 13/187,672

(22) Filed: Jul. 21, 2011

(65) Prior Publication Data
US 2011/0275796 A1 Nov. 10, 2011

Related U.S. Application Data

(63) Continuation of application No. 11/490,543, filed on Jul. 21, 2006, now abandoned.

(30) Foreign Application Priority Data

Jul. 21, 2005 (EP) .................................. 05090214

(51) Int. Cl.
*C07J 71/00* (2006.01)
(52) U.S. Cl.
USPC .............................................. 540/72
(58) Field of Classification Search
None
See application file for complete search history.

(56) References Cited

U.S. PATENT DOCUMENTS

| 5,569,652 | A | 10/1996 | Beier et al. |
| 6,121,465 | A | 9/2000 | Mohr |
| 7,319,154 | B2 | 1/2008 | Seilz et al. |
| 7,585,971 | B2 | 9/2009 | Costantino et al. |
| 8,227,596 | B2 | 7/2012 | Costantino |
| 2004/0220158 | A1 | 11/2004 | White et al. |
| 2008/0207575 | A1 | 8/2008 | Costantino et al. |

FOREIGN PATENT DOCUMENTS

| EP | 0075 189 | 3/1983 |
| EP | 1571153 | 9/2005 |
| IT | 2004-MI2338 | 3/2005 |
| WO | WO 90/14344 | 11/1990 |
| WO | WO 98/06738 | 2/1998 |
| WO | WO 2006/061309 | 6/2006 |

OTHER PUBLICATIONS

Bittler, D. et al., "Synthesis of Spriorenone—A Novel Highly Active Aldosterone Antagonist," Angewante Chemie International Edition, 1982, vol. 21 No. 9, pp. 696-697, XP002047531.

Nickisch, K. et al., "Aldosterone Antagonists 2. New 7-Alpha Acetylthio-15 16-Methylenespirolactones," Journal of Medicinal Chemistry, 1987, vol. 30 No. 8, pp. 1403-1409, XP002367543.

(Continued)

*Primary Examiner* — Noble Jarrell
(74) *Attorney, Agent, or Firm* — Millen, White, Zelano & Branigan, P.C.

(57) ABSTRACT

This invention relates to processes for the production of 3-oxo-pregnane-21,17-carbolactones of formula II

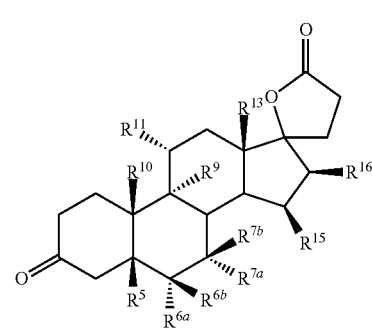

as well as 3-oxo-pregn-4-ene-21,17-carbolactones of formula III

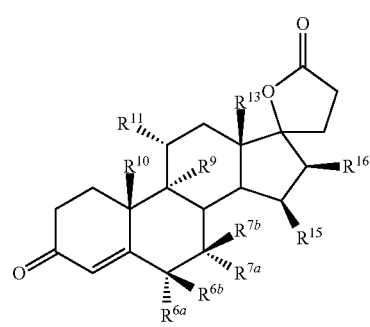

by the metal-free oxidation of 17-(3-hydroxypropyl)-3,17-dihydroxyandrostanes of formula I

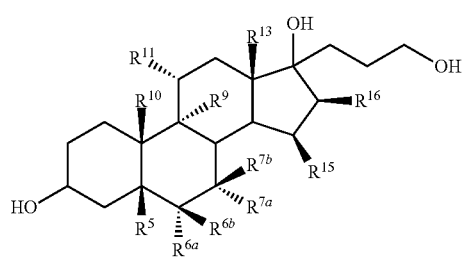

In addition, the invention relates to the dichloromethane hemisolvate of 6β,7β;15β,16β-dimethylene-3-oxo-17α-pregnan-5β-ol-21,17-carbolactone (IV) as such as well as to a process for the production of drospirenone.

38 Claims, No Drawings

(56) References Cited

OTHER PUBLICATIONS

Zhang et al., "Asymmetric Dihydroxilation-Haloetherification Strategy for the Synthesis of Tetrahydrofuran-Containing Acetogenins," Journal of Organic Chemistry. American Chemical Society, 1998, vol. 63 No. 6, pp. 2049-2052, XP002104971.

Anelli, P.L. et al., "Oxidation of Diols with Alkali Hypochlorites Catalyzed by Oxammonium Salts Under 2-Phase Conditions," Journal of Organic Chemistry, American Chemical Society, Jun. 9, 1989, vol. 54 No. 12, pp. 2970-2972, XP000025425.

Preliminary Amendment of U.S. Appl. No. 11/792,465, Petition to Make Special of Sep. 10, 2008, Information Disclosure Statement of Feb. 13, 2009, all from U.S. Appl. No. 11/792,465, filed Jun. 4, 2007.

Opposition by Industriale Chemica against EP 1746101 (corresponding to this application), pp. 1-16, with attachments D3-D6; filed Mar. 6, 2009.

Merbouh, N., et al., "Preparation of Tetramethylpoperidine-1-Oxoammonium Salts and Their Use as Oxidants in Organic Chemistry. A Review," Organic Preparations and Procedures International 36(1), pp. 3-31 (2004).

Office Action of Dec. 30, 2009, issued in U.S. Appl. No. 11/792,465—8 pages.

Responsive Amendment of Mar. 24, 2010, filed in U.S. Appl. No. 11/792,465—32 pages.

Priority Document of WO 2006/061309—MI 2004 A 002338 Milan, Code 15, Dated Dec. 6, 2004—Applicant(s) Industriale Chimica S.R.L., Milan Italy, Process for the Preparation of Drospirenone.

PCT Written Opinion of the International Searching Authority (PCT Rule 43*bis*.1), Applicant(s) Schering Aktiengesellschaft—International Application No. PCT/EP2006/007287 filed Jul. 20, 2006, priority date Jul. 21, 2005.

Semmelhack, M.F., et al., "Oxidation of Alcohols to Aldehydes with Oxygen and Cupric Ion, Mediated by Nitrosonium Ion," J. Am. Chem. Soc., 1984, 106, 3374.

Miyazawa, T., et al., "Oxidation of Diols with Oxoaminium Salts," J. Org. Chem., 1985, 50, 3930-3931.

Office Action dated Jun. 18, 2010, issued in U.S. Appl. No. 11/792,465 (7 pages).

Amendment dated Aug. 4, 2010 submitted in U.S. Appl. No. 11/792,465 (15 pages).

Supplemental Amendment dated Oct. 14, 2010 submitted in U.S. Appl. No. 11/792,465 (15 pages).

Suggestion for Interference Pursuant to 37 CFR § 41.202 dated Oct. 15, 2010 submitted in U.S. Appl. No. 11/792,465 (23 pages).

Notice of Opposition to a European Patent issued in opposition to EP 1746101 B1, posted May 8, 2009 (dated May 6, 2009) (5 pages).

Anelli, P.L., et al., "Oxidation of Diols with Alkali Hypochlorites Catalyzed by Oxammonium Salts under Two-Phase Conditions," J. Org. Chem. 1989, 54, 2970-2972.

Bruckner, et al., "Preparation of Tetramethylpiperidine-1-Oxoammonium Salts and Their Use as Oxidants in Organic Chemistry. A Review," Dept. of Chemistry, University of Connecticut, Unit 3060, pp. 3-31, Jun. 9, 1989.

deNooy, A.E.J., et al., "On the Use of Stable Organic Nitroxyl Radicals for the Oxidation of Primary and Secondary Alcohols," Synthesis, Oct. 1996, pp. 1153-1174.

Opposition Against European Patent No. EP 1 828 222 B1, Application No. 05 819 134.7, dated Sep. 15, 2011, pp. 1-13.

Response to Notice of Opposition Against European Patent No. EP 1 828 222 B1, Application No. 05 819 134.7, dated May 8, 2012, pp. 1-10.

English translation of Document D5 in Response to Notice of Opposition Against European Patent No. EP 1 828 222 B1, Application No. 05 819 134.7, (Jul. 3, 2012), 14 pages.

Notice of Docketing Appeal No. 12-1511. Dated: Jul. 11, 2011.

Notice of Appeal to Clerk of the Court United States Court of Appeals for the Federal Circuit and Letters.

Decision on Motions in Interference No. 105,788.

Judgment on Merits in Interference No. 105,788.

Decision on Request for Rehearing in Interference No. 105,788.

Decision—Motions issued from the Patent Trial and Appeal Board ("Board") in the United States Patent and Trademark Office dated Jan. 4, 2012. Paper 154. (21 pages).

Judgment—Merits issued from the Patent Trial and Appeal Board ("Board") in the United States Patent and Trademark Office dated Jan. 4, 2012. Paper 155. (3 pages).

Decision on Costantino Request for Rehearing issued from the Patent Trial and Appeal Board ("Board") in the United States Patent and Trademark Office (affirming the original Decision/Judgment) dated Mar. 28, 2012. Paper 160. (11 pages).

Judgment issued from the United States Court of Appeals for the Federal Circuit affirmed the decision of the Board in favor of Patentees/Reissue applicants dated Mar. 12, 2013. (3 pages).

PROCESS FOR THE PRODUCTION OF 3-OXO-PREGN-4-ENE-21,17-CARBOLACTONES BY THE METAL-FREE OXIDATION OF 17-(3-HYDROXYPROPYL)-3,17-DIHYDROXYANDROSTANES

This application is a continuation of U.S. patent application Ser. No. 11/490,543, filed Jul. 21, 2006 now abandoned, which is incorporated by reference herein.

This invention relates to processes for the production of 3-oxo-pregnane-21,17-carbo-lactones as well as 3-oxo-pregn-4-ene-21,17-carbolactones, in particular processes for the production of 3-oxo-17α-pregnane-21,17-carbolactones as well as 3-oxo-17α-pregn-4-ene-21,17-carbolactones. In addition, the invention relates to the dichloro-methane hemisolvate of 6β,7β;15β,16β-dimethylene-3-oxo-17α-pregnan-5β-ol-21,17 carbolactone.

Examples of pharmacologically active steroid-21,17-carbolactones are eplerenone (9α,11α-epoxy-7α-methoxycarbonyl-3-oxo-17α-pregn-4-ene-21,17-carbolactone), drospirenone (6β,7β;15β,16β-dimethylene-3-oxo-17α-pregn-4-ene-21,17-carbolactone), spironolactone (7α-acylthio-3-oxo-17α-pregn-4-ene-21,17-carbolactone), canrenone (3-oxo-17α-pregna-4,6-diene-21,17-carbolactone), and prorenone (6β,7β-methylene-3-oxo-17α-pregna-4,6-diene-21,17-carbolactone).

The build-up of the steroid-21,17-spirolactone can be carried out by oxidation of the corresponding 17-hydroxy-17-(3-hydroxypropyl) steroid

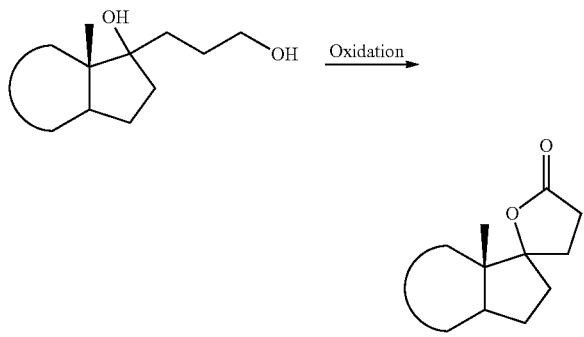

with suitable oxidizing agents such as chromic acid (Sam et al. J. Med. Chem. 1995, 38, 4518-4528), pyridinium chlorochromate (EP 075189), pyridinium dichromate (Bittler et al; Angew. Chem. [Applied Chem.] 1982, 94, 718-719; Nickisch et al. Liebigs Ann. Chem. 1988, 579-584), or potassium bromate in the presence of a ruthenium catalyst (EP 918791). The clearly pronounced formation of by-products by a number of secondary reactions is disadvantageous in the oxidation process of the prior art with chromium(VI) derivatives, by which the isolation of the pure product is hampered and the yield is reduced. The by-product profile is improved namely by the ruthenium-catalyzed oxidation (EP 918791), and thus also the yield increases. The use of transition metals in the production of pharmaceutical active ingredients, however, is generally associated with the drawback that the removal of heavy metal traces is already connected with an elevated expense. Moreover, large amounts of heavy metal-containing wastes accumulate in the production, and said wastes can be removed only in an intensive and costly way.

The object of this invention therefore consists in making available an alternate process for the production of 3-oxo-pregnane-21,17-carbolactones as well as 3-oxo-pregn-4-ene-21,17-carbolactones from the corresponding 17-(3-hydroxypropyl)-3,17-dihydroxy-androstanes that makes it possible to produce the target compounds with a higher yield and purity.

This object was achieved according to the invention in that the 17-(3-hydroxypropyl)-3,17-dihydroxyandrostanes of general formula I

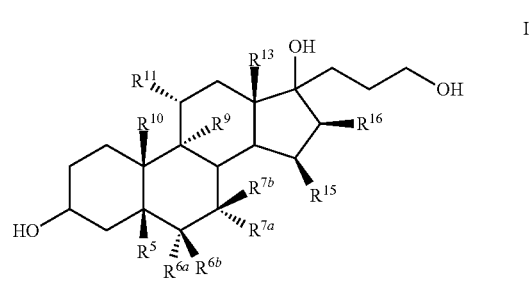

in which $R^5$ is hydrogen, hydroxy;

$R^{6a}$ is hydrogen, together with $R^5$ a double bond, or together with $R^{7a}$ a —$CH_2$ group;

$R^{6b}$ is hydrogen, together with $R^{7b}$ a —$CH_2$ group or a double bond;

$R^{7a}$ is hydrogen, $C_1$-$C_4$-alkyl, $C_1$-$C_4$-alkoxycarbonyl, $C_1$-$C_4$-thioacyl or together with $R^{6a}$ a —$CH_2$ group;

$R^{7b}$ is hydrogen, or together with $R^{6b}$ a —$CH_2$ group;

$R^9$ is hydrogen, together with $R^{11}$ a double bond, or together with $R^{11}$ an epoxy group —O—;

$R^{10}$ is hydrogen, methyl, or ethyl;

$R^{11}$ is hydrogen, together with $R^9$ a double bond or together with $R^9$ an epoxy group —O—;

$R^{13}$ is hydrogen, methyl or ethyl;

$R^{15}$ is hydrogen, $C_1$-$C_4$-alkyl, together with $R^{16}$ a —$CH_2$ group or a double bond, $R^{16}$ is hydrogen, together with $R^{15}$ a —$CH_2$ group or a double bond, are reacted with an organic or inorganic hypochlorite as an oxidizing agent in the presence of catalytic amounts of a 2,2,6,6-tetramethylpiperidine-N-oxide derivative to form the 3-oxo-pregnane-21,17-carbolactones of Formula II

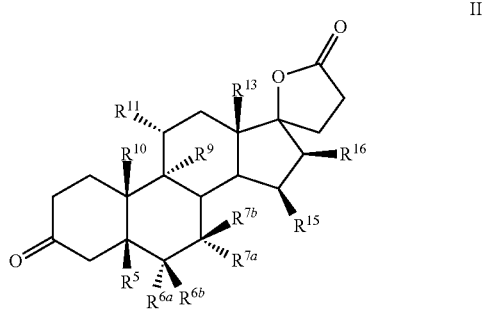

If $R^5$ is a hydroxy group, the compounds of formula II can be converted in the presence of an acid at pH<5 with water being eliminated into compounds of formula III

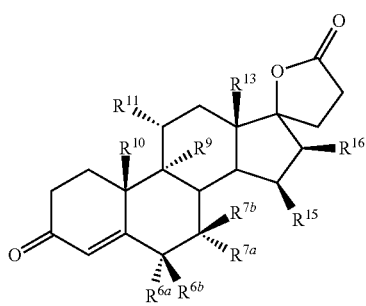

III

Metal-free oxidations of alcohols to the corresponding aldehydes, ketones, carboxylic acids, lactols, and lactones are collectively referred to in the survey article of W. Adam et al., Chem. Rev. 2001, 101, 3499-3548. Metal-free oxidations in the presence of 2,2,6,6-tetramethylpiperidine-N-oxide (TEMPO) are described by van Bekkum et al. in Synthesis 1996, 1153-1174.

Primary alcohols can be oxidized to aldehydes with sodium bromite ($NaBrO_2$) or calcium hypochlorite [Ca $(OCl_2)$] in the presence of TEMPO derivatives [S. Torii et al. J. Org. Chem. 1990, 55, 462-466]. Sodium hypochlorite (NaOCl) can also be used as an oxidizing agent (Org. Synth. 69, 212).

The oxidation of secondary alcohols to ketones and in particular the oxidation of primary alcohols to carboxylic acids (or with suitable diols to lactones) requires a co-catalyst (P. L. Anelli et al., J. Org. Chem. 1987, 52, 2559-2562). As a co-catalyst, a bromide (generally KBr or NaBr) is used. The addition of bromide ions can be useful even in the oxidation of primary alcohols to aldehydes (P. L. Anelli et al., J. Org. Chem. 1987, 52, 2559-2562).

The danger of the formation of bromine-containing by-products under oxidative conditions is disadvantageous in the use of bromides as co-catalysts. This oxidation method is especially suitable for the oxidation of primary alcohols to the corresponding aldehydes.

Without the addition of bromide, the TEMPO-catalyzed oxidation of secondary alcohols to the corresponding ketones requires higher excesses of hypochlorite [3-4 molar equivalents of $Ca(OCl)_2$, thus 6-8 molar equivalents of $OCl^-$; (S. Tori et al. J. Org. Chem. 1990, 55, 462-466)].

The oxidative lactonization of 1,4-diols proceeds in many stages via the aldehyde, which first forms lactol in an intermediate stage; the quasi-secondary hydroxy group of said lactol must then be further oxidized. The oxidative lactonization of 1,4-diols therefore requires still harder conditions (at least equimolar amounts of the TEMPO derivative (J. M. Bobbitt et al., J. Org. Chem. 1991, 56, 6110-6114) or other oxidizing agents in connection with increased amounts of the TEMPO catalyst (J. Einhorn, J. Org. Chem. 1996, 61, 7452-7454; in the presence of a bromide addition: S. D. Rychnovsky, J. Org. Chem. 1999, 64, 310-312; in the presence of bromide ions produced in situ from the oxidizing agent sodium bromite: S. Torii, J. Org. Chem. 1990, 55, 462-466). In view of the prior art, it was therefore surprising that oxidative lactonization on the D-ring and the oxidation of the secondary 3-hydroxy group of the 17-(3-hydroxypropyl)-3, 17-dihydroxyandrostanes of general formula I (altogether three oxidation stages) can be performed successfully at the same time under mild conditions in the presence of catalytic amounts of TEMPO derivatives. In addition, it was surprising that the process according to the invention can be performed with only 1.0 to 2.0 equivalents of hypochlorite per oxidation stage, thus altogether 3.0 to 6.0 molar equivalents of hypochlorite quite without the co-catalytic bromide additions.

The process according to the invention is performed with a total of at least 3 molar equivalents of alkali hypochlorite, organic hypochlorite or at least 1.5 molar equivalents of alkaline-earth hypochlorite as oxidizing agent; preferably with 3-6 molar equivalents of alkali hypochlorite, or 1.5-3 molar equivalents of alkaline-earth hypochlorite, especially preferably 3-4 molar equivalents of alkali hypochlorite or 1.5-2 molar equivalents of alkaline-earth hypochlorite, most preferably 3.0-3.5 molar equivalents of alkali hypochlorite on 1.5-1.75 molar equivalents of alkaline-earth hypochlorite.

The concentration of the aqueous hypochlorite solution during the oxidation is preferably adjusted such that it is 0.8 to 1.1 mol of hypochlorite/kg.

Sodium hypochlorite, potassium hypochlorite, calcium hypochlorite or tert-butyl hypochlorite are preferably used as oxidizing agents.

The 2,2,6,6-tetramethylpiperidine-N-oxide derivatives (TEMPO derivatives) are used in catalytic amounts, whereby the amount is preferably 1-5 mol %, especially preferably 1-1.5 mol %.

Suitable TEMPO derivatives are, i.a., the 2,2,6,6-tetramethylpiperidine-N-oxide (TEMPO), the 4-methoxy-2,2,6,6-tetramethylpiperidine-N-oxide (4-MeO-TEMPO) as well as the 4-benzyloxy-2,2,6,6-tetramethylpiperidine-N-oxide (4-BnO-TEMPO). TEMPO is preferably used according to this invention, especially preferably in an amount of 1-5 mol %, quite especially preferably 1-1.5 mol %.

The oxidation is carried out in an organic solvent or in a two-phase solvent-water mixture, whereby the solvent is selected such that both the TEMPO derivative and the compounds of formula I can be well dissolved therein.

The reaction is preferably performed in a two-phase system. The process according to the invention is quite preferably performed in a dichloromethane-water mixture.

The oxidation is performed according to the invention at a temperature of 0 to 20° C., e.g., 0 to 15° C., preferably at 10-20° C.

During the oxidation, the pH of the reaction solution is to be at least 8.0; preferably 8.5 to 10.0; especially preferably 9.0 to 9.5.

The pH can suitably be adjusted with a suitable Brönsted acid, such as organic acids (e.g., acetic acid) or inorganic acids (HCl, $H_2SO_4$, $H_3PO_4$) or acid salts of multivalent acids (bicarbonates, hydrogen sulfates, hydrogen phosphates, etc.). Alkali bicarbonates, especially preferably potassium bicarbonate, are preferably used.

The oxidation reaction is brought to a halt by adding a reducing agent to quench excess hypochlorite reagent. For this purpose, any reducing agent with corresponding redox potential that is known to one skilled in the art is suitable. An aqueous alkali hydrogen sulfite solution is preferably used according to this invention. Sodium or potassium hydrogen sulfite (NaHSO$_3$ or KHSO$_3$), the aqueous solution of sodium or potassium disulfite (Na$_2$S$_2$O$_5$ or K$_2$S$_2$O$_5$) is especially preferably used.

If, in the reaction mixture, the excess hypochlorite reagent at pH<5 is quenched thus without the addition of a base or a basic buffer, or in the presence of a further acid addition, the 3-oxo-pregnane-21,17-carbolactones of formula II (if R$^5$=OH) thus eliminate water, and equally the 3-oxo-pregn-4-ene-21,17-carbolactones of formula III are formed in the reaction mixture. The completion of the oxidation reaction at a pH of less than 5 makes possible the production of compounds of formula III in a one-pot process.

If, in the reaction mixture, the excess hypochorite reagent is quenched with the addition of a base or a basic buffer at pH>5, the 3-oxo-pregnane-21,17-carbolactones of formula II can be isolated. The completion of the oxidation reaction at a pH of more than 5 makes possible the specific production of compounds of formula II.

Since in the case R$^5$=OH the solubility of the compounds of formula II in comparison to the compounds of formula III in organic solvents is lower, the specific isolation of the compounds of formula II as an intermediate on the path to compounds of formula III offers the special advantage of the possibility of a more effective purification (e.g., by crystallization). The purified intermediates can be reacted according to the methods that are known in the literature with a suitable acid (such as, e.g., sulfuric acid, hydrochloric acid, para-toluenesulfonic acid, etc.) to form compounds of formula III (EP 0918791), thus advantageously lessening impurities in such formula III compounds, especially when R$^5$=OH.

To adjust the pH, any suitable inorganic or organic base or any suitable buffer or any suitable buffer system can be used. The base or buffer is preferably added mixed or in parallel to the reaction mixture with the reducing agent.

According to this invention, sodium phosphate (Na$_3$PO$_4$) is preferably used as a basic buffer.

17-(3-Hydroxypropyl)-3,17-dihydroxyandrostanes of general formula I can be obtained, e.g., starting from the correspondingly substituted 3-hydroxy-17-ketoandrostanes by the addition of propargyl alcohol at C-17 and subsequent hydrogenation of the triple bond (EP 918791, EP 51143, DE 3026783) or as described by N. W. Atwater in J. Org. Chem. 1961, 26, 3077 and in U.S. Pat. No. 4,069,219 or in the documents cited therein.

The corresponding 3-hydroxy-17-ketoandrostanes can be produced in turn from the correspondingly substituted 3-hydroxyandrost-5-en-17-one (EP 51143, DE 3026783).

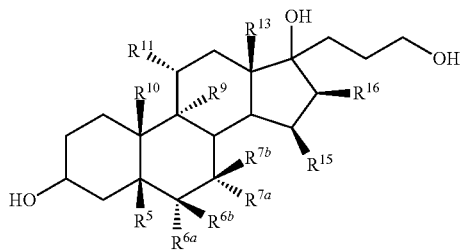

I oxidation

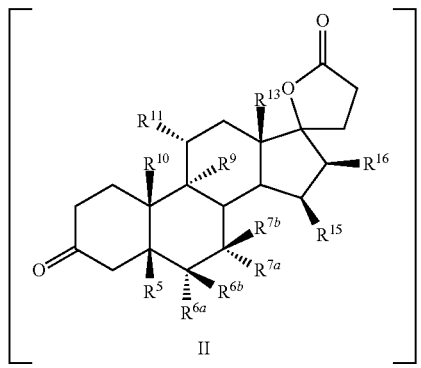

work-up at pH < 5
R$^5$ = OH work-up at pH > 5

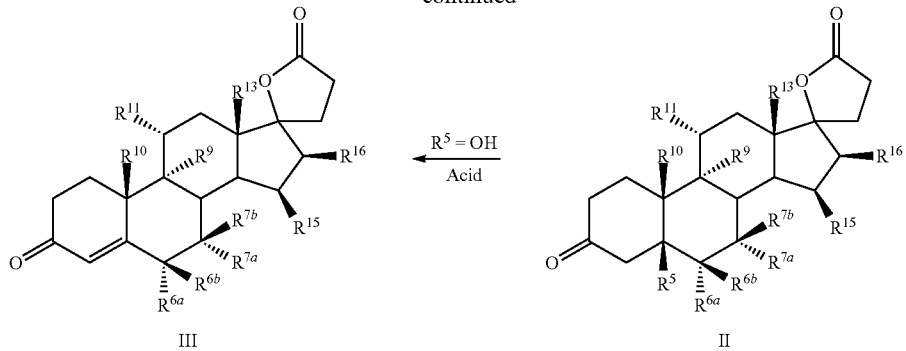

The process according to the invention is suitable especially for the production of 3-oxo-17α-pregnane-21,17-carbolactones of formula IIa

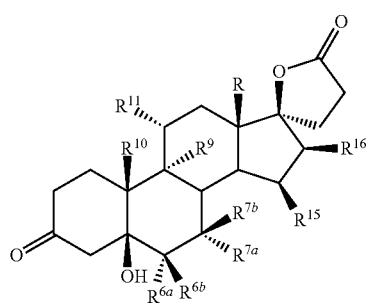

IIa as well as 3-oxo-17α-pregn-4-ene-21,17-carbolactones of formula IIIa,

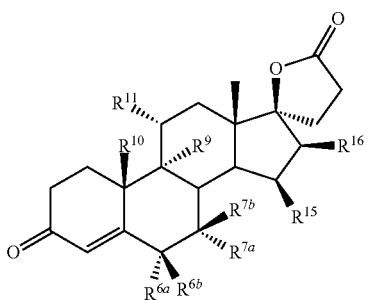

IIIa in which the substituents R have the following meaning:
$R^{6a}$ is hydrogen or together with $R^{7a}$ a —CH$_2$ group;
$R^{6b}$ is hydrogen, together with $R^{7b}$ a —CH$_2$ group, or a double bond;
$R^{7a}$ is hydrogen, $C_1$-$C_4$-alkoxycarbonyl, or $C_1$-$C_4$-thioacyl;
$R^{7b}$ is hydrogen, or together with $R^{6b}$ a —CH$_2$ group,
$R^9$ is hydrogen, together with $R^{11}$ a double bond or together with $R^{11}$ an epoxy group —O—;
$R^{10}$ is hydrogen, or methyl;
$R^{11}$ is hydrogen, together with $R^9$ a double bond or together with $R^9$ an epoxy group —O—;
$R^{15}$ is hydrogen, together with $R^{16}$ a —CH$_2$ group or a double bond;
$R^{16}$ is hydrogen, together with $R^{15}$ a —CH$_2$ group or a double bond;
whereby as starting materials, the 17-(3-hydroxypropyl)-3,17-dihydroxyandrostanes of general formula Ia

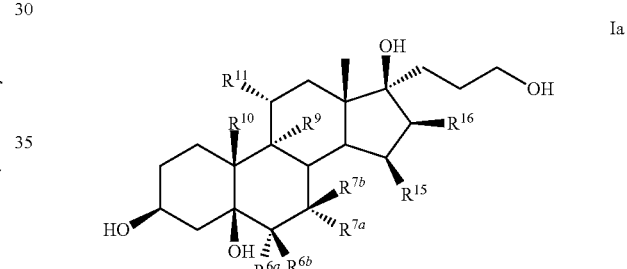

Ia are used.
The process according to the invention for the production of compounds of formulas IIa and IIIa,
in which
$R^{6a}$, $R^{7a}$, $R^9$, $R^{11}$ are hydrogen;
$R^{6b}$ and $R^{7b}$ together are a —CH$_2$ group;
$R^{10}$ is methyl;
$R^{15}$ and $R^{16}$ together are a —CH$_2$ group;
thus compounds IIb as well as IIIb, whereby the compound of formula Ib is used as a starting material is quite especially suitable.

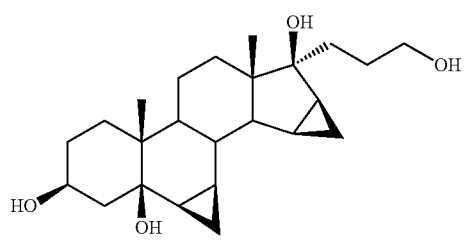

Ib

↓ oxidation

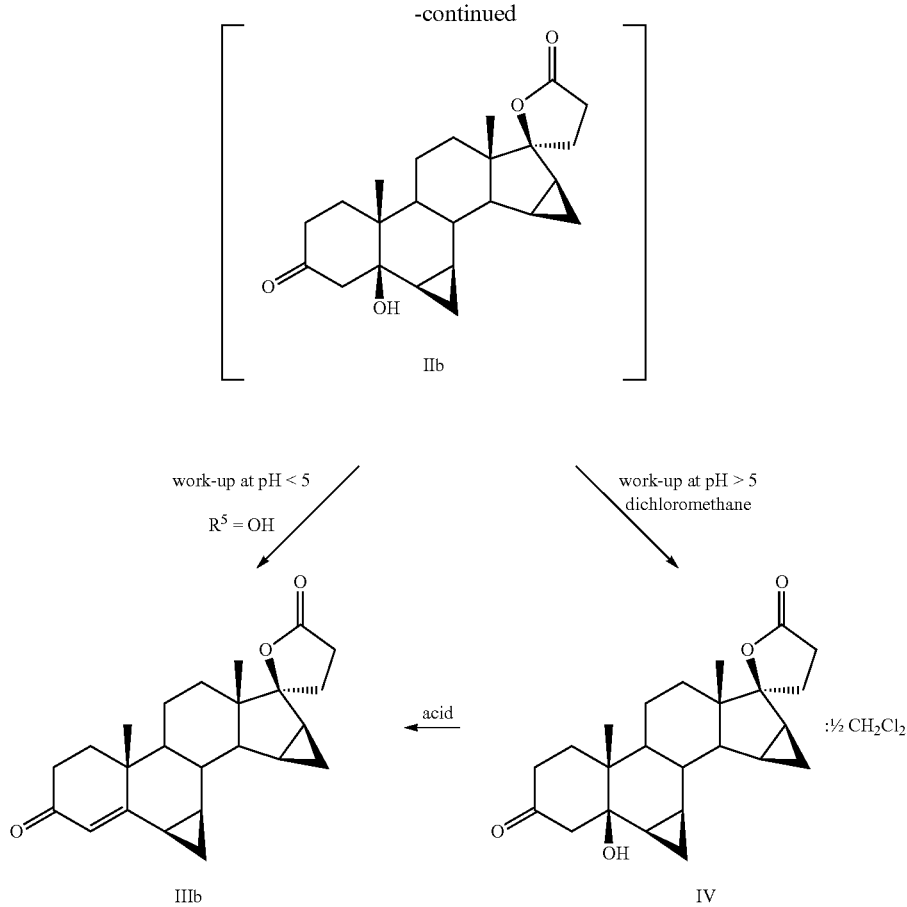

Another aspect of this invention is the poorly soluble dichloromethane-hemisolvate IV that is formed, surprisingly enough, from compound IIb when the process according to the invention is performed in dichloromethane and is worked up, basic, at pH>5. During the oxidation, this poorly soluble product precipitates, and thus the influence of the oxidizing agent and thus possible further reactions, which can result in the formation of by-products, are evaded, thereby providing the hemisolvate IV in good purity.

The dichloromethane-hemisolvate IV is distinguished by a strict and constant melting point, which is 121° C. while compound IIb melts at 188° C. DSC (Differential Scanning calorimetry) measurements have shown that compound IV is stable up to the melting point.

After the reaction is completed, the precipitation of compound IV from the reaction solution by adding a non-polar solvent, preferably an ether, especially preferably diisopropyl ether, is completed. The non-polar oxidation and elimination products that are produced with the oxidation remain largely dissolved in the ether-dichloromethane mixture, which makes possible an extremely slight isolation of the compound IV at a high purity.

In this way, compound IV with a yield of 82% is obtained. The thus obtained product contains no more than 6% steroidal contaminants and can easily be reacted without further purification according to known methods with a suitable acid to form drospirenone IIIb (EP 918791). The synthesis variant that runs through the isolated compound IV offers the additional advantage of a considerably higher total yield at IIIb by a simpler and more effective purification in the final stage. The total yield at IIIb is 77%, around 7% higher than according to the Ru-catalyzed oxidation process and subsequent water elimination and even around 21% higher than according to the one-pot process according to EP 075189 (Tab. 1).

The terms "isolation" or "isolated" and the like as used herein mean separation of the subject compound (e.g., that of the Formula II) at a pH>5 (preferably in the presence of methylene chloride) from the reaction solution in which it is prepared; or separation of the subject compound by crystallization and/or precipitation; or separation (e.g., substantially) from the non-polar oxidation or elimination products in the reaction solution in which the compound of Formula II is prepared; or separation from the reaction solution in a form whereby no more than 6% of steroidal contaminants are present in the resultant product (based on total weight thereof).

As an alternative, Ib can be oxidized to IIb and converted directly to IIIb in the same pot by the reaction mixture being worked up under acidic conditions at pH<5.

TABLE 1

Comparison of the Yields of the Process According to the Invention Compared to the Process of the Prior Art

| Process | Yield (% of Theory) | | |
|---|---|---|---|
| | Ib → IIb | IIb → IIIb | Total (Ia → IIIb) |
| Process According to the Invention | 82 (in the form of IV) | 94 | 77 |

TABLE 1-continued

Comparison of the Yields of the Process According to
the Invention Compared to the Process of the Prior Art

| Process | Yield (% of Theory) | | |
|---|---|---|---|
| | Ib → IIb | IIb → IIIb | Total (Ia → IIIb) |
| Ru-Catalyzed Oxidation According to EP 918791 | 75 | 94 | 70 |
| $CrO_3$ Oxidation According to EP 075189* | not isolated | not isolated | 56 |

*See Table on page 7 EP 918791

This invention is explained in more detail based on the examples below, without being limited thereto.

Production Process

General Operating Procedure 1 (GOP1): Synthesis of Compounds of Formula II 76.9 mmol of a compound of formula I is dissolved or suspended in 135 ml of dichloromethane. First, 0.15 g (1 mmol) of TEMPO is added to the mixture at 15° C. The addition of a solution that consists of 134 g of a 15.25% aqueous sodium hypochlorite solution (230.7 mmol) and 8.20 g (82 mmol) of potassium bicarbonate in 114 ml of water is carried out, whereby a pH-value of 9.1 is set. After the reaction is completed, the excess oxidizing agent is quenched at 15° C. by adding an aqueous solution that consists of 12.5 g (76.5 mmol) of sodium phosphate and 10.6 g (55.8 mmol) of sodium disulfite ($Na_2S_2O_5$) and 121 ml of water.

The product of formula II is isolated from the organic phase by being precipitated from the reaction solution by adding 240 ml of diisopropyl ether, continuing to be stirred for 3 hours at 25° C., being filtered off and dried. As an alternative, the product that is already partially precipitated during the reaction depending on solubility in dichloromethane can be dissolved again by adding dichloromethane, and the organic phase is separated and redistilled in diisopropyl ether. The product that is precipitated in this case is filtered off with 300 ml of water, washed and dried.

General Operating Procedure 2 (GOP2): Synthesis of Compounds of Formula III in a One-Pot Process 76.9 mmol of a compound of formula I is dissolved or suspended in 135 ml of dichloromethane. First, 0.15 g (1 mmol) of TEMPO is added at 15° C. to the mixture. The addition of a solution that consists of 134 g of a 15.25% aqueous sodium hypochlorite solution (230.7 mmol) and 8.20 g (82 mmol) of potassium bicarbonate in 114 ml of water is carried out, whereby a pH-value of 9.1 is set. After the reaction is completed, the excess oxidizing agent is quenched at 15° C. by adding an aqueous solution of 10.6 g (55.8 mmol) of sodium disulfite ($Na_2S_2O_5$) in 121 ml of water.

The pH of the reaction solution is set at pH<5 by adding dilute, aqueous sulfuric acid, and stirring is continued at room temperature until the reaction is complete.

The isolation of the product of formula III is carried out analogously to the isolation of the compounds of formula II according to GOP1, whereby the neutral washed organic phase is redistilled on diisopropyl ether. The product that is precipitated in this case is filtered off, washed with 300 ml of water and dried.

General Operating Procedure 3 (GOP3): Synthesis of Compounds of Formula III Starting from Compounds of Formula II, in which $R^5$=OH:

0.1 mol of a compound of formula II, in which $R^5$=OH, obtained according to GOP1, is suspended in 65 ml of tetrahydrofuran or dioxane and acidified to a pH of 1 by adding 5 ml of 20% sulfuric acid. At room temperature, stirring of the reaction mixture is continued until dehydration is completed.

The isolation of the product of formula III is carried out by precipitation by means of the addition of 90 ml of water. The precipitated product is filtered off with water, washed neutral and dried.

EXAMPLE 1

6β,7β;15β,16β-Dimethylene-3-oxo-17α-pregnan-5β-ol-21,17-carbolactone-dichloromethane hemisolvate (IV)

According to GOP1, 30 g (0.0769 mol) of 17α-(3-hydroxypropyl)-6β,7β;15β,16β-dimethylene-androstane-3β,5β,17β-triol is reacted.

During the reaction, the product 6β,7β;15β,16β-dimethylene-3-oxo-17α-pregnan-5β-ol-21,17-carbolactone accumulates in the form of its dichloromethane hemisolvate. After excess oxidizing agent is destroyed and after working-up according to GOP1, 27 g of 6β,7β;15β,16β-dimethylene-3-oxo-17α-pregnan-5-ol-21,17-carbolactone-dichloromethane hemisolvate (0.0630 mol)=82% of theory is isolated.

$[\alpha]_D^{20}$=−61° (c=1.0; $CHCl_3$); melting point=121° C.;
$^1$H-NMR (400 MHz, $CDCl_3$): δ=0.52 (q J=5.5 Hz, 1H, 21 α-H [of the 15,16-methylene bridge]), 0.68-0.78 (m, 2H, 20-H [of the 6,7-methylene bridge]), 0.89-0.97 (m, 1H, 6-H), 0.93 (s, 3H, 19-H), 0.99 (s, 3H, 18-H), 1.19-1.52 (m, 7H), 1.54-1.85 (m, 6H), 1.92 (dd J=3.8 and 11.8 Hz, 1H, 14-H), 2.06-2.16 (m, 1H, 22-H), 2.17-2.27 (m, 1H, 2α-H), 2.32-2.69 (m, 5H), 2.96 (d J=15.6 Hz, 1H, 4α-H), 5.30 (s, 1H, $CH_2Cl_2$).
$^{13}$C-NMR (400 MHz, $CDCl_3$): δ=9.97 ($CH_2$, C-21), 11.63 ($CH_2$, C-20), 16.74 (CH, C-15), 16.79 (CH, C-7), 17.29 ($CH_3$, C-19), 19.83 ($CH_3$, C-18), 21.75 ($CH_2$, C-11), 24.31 (CH, C-16), 24.76 (CH, C-6), 29.35 ($CH_2$, C-23), 30.70 ($CH_2$, C-22), 33.96 (CH, C-8), 34.47 ($CH_2$, C-1), 36.26 ($CH_2$, C-2), 37.31 ($CH_2$, C-12), 40.25 (C, C-10), 41.81 (C, C-13), 47.59 (CH, C-9), 52.18 (CH, C-14), 53.44 ($CH_2Cl_2$), 53.48 ($CH_2$, C-4), 75.57 (C, C-5), 96.24 (C, C-17), 176.63 (C, C-24), 210.56 (C, C-3).
MS (EI, 70 eV) m/e=384 ($M^+$); m/e=366 ($M^+$-$H_2O$); m/e=314 ($M^+$-$C_4H_6O$); m/e=111 ($C_7C_{11}O^+$); m/e=91 ($C_6H_{11}O^+$); m/e=55 ($C_3H_3O^+$); m/e=43 ($C_2H_3O^+$).
IR: θ=3483 $cm^{-1}$ (OH); θ=1757 $cm^{-1}$ (C=O, lactone); θ=1708 $cm^{-1}$ (C=O); θ=1200 $cm^{-1}$ (O—C=O); θ=1011 $cm^{-1}$ (C—O)

EXAMPLE 2

6β,7β;15β,16β-Dimethylene-3-oxo-17α-preg-4-ene-21,17-carbolactone (IIIb)

According to GOP2, 30 g (0.0769 mol) of 17α-(3-hydroxypropyl)-6β,7β;15β,16β-dimethylene-androstane-3β,5β,17β-triol is reacted. After excess oxidizing agent is destroyed according to GOP2, the reaction mixture is acidified with 10% sulfuric acid solution to a pH of 1 and stirred for 30 minutes at 25° C. After working-up according to GOP2, 21.5 g of 6β,7β;15β,16β-dimethylene-3-oxo-17α-preg-4-ene-21,17-carbolactone (0.059 mol)=76.7% of theory is isolated.

$[\alpha]_D^{22} \approx -182°$ (c=0.5 CHCl$_3$); melting point=201.3° C.; UV (MeOH): $\epsilon_{265}$=19,000; most important $^1$H-NMR data (CDCl$_3$): δ=0.40-0.67 (m, 1H, cyclopropyl H), 1.01 (s, 3H, 18-H), 1.11 (s, 3H, 19-H), 6.04 (s, 1H, 4-H) (D. Bittler, H. Hofineister, H. Laurent, K. Nickisch, R. Nickolson, K. Petzoldt, R. Wiechert; Angew. Chem. Int. Ed. Engl. 1982, 21, 696-697];

MS (EI, 70 eV) m/e=366 (M$^+$); m/e=338 (M$^+$-CO); m/e=351 (M$^+$-CH$_3$); significant fragments: m/e=111; m/e=136; m/e=199, m/e=217; m/e=242; m/e=255; m/e=268; m/e=293 [Interpretation: See W. Krause, G. Kuehne; Steroids 1982, 40, 81-90].

EXAMPLE 3

6β,7β:15β,16β-dimethylene-3-oxo-17α-preg-4-ene-21,17-carbolactone (IIIb)

According to GOP3, 30 g (70.25 mmol) of 6β,7β:15β,16β-dimethylene-3-oxo-17α-pregnane-5β-ol-21,17-carbolactone dichlormethane hemisolvat (from Example 1) is reacted to yield 24.30 g of drospirenone (yield: 94.5%).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 05090214.7, filed Jul. 21, 2005 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of a 3-oxo-pregn-4-ene-21,17-carbolactone of formula III:

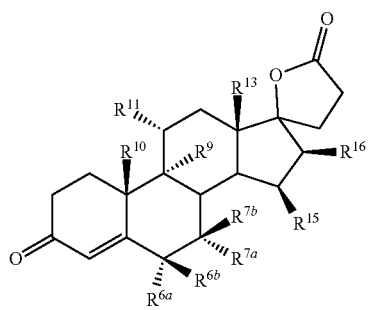

in which $R^{6a}$ is hydrogen or together with $R^{7a}$ a —CH$_2$ group;
$R^{6b}$ is hydrogen or together with $R^{7b}$ a —CH$_2$-group;
$R^{7a}$ is hydrogen, C$_1$-C$_4$-alkyl, C$_1$-C$_4$-alkoxycarbonyl, C$_1$-C$_4$-thioacyl or together with $R^{6a}$ a —CH$_2$-group;
$R^{7b}$ is hydrogen or together with $R^{6b}$ a —CH$_2$-group;
$R^9$ is hydrogen, together with $R^{11}$ a double bond, or together with $R^{11}$ an epoxy group —O—;
$R^{10}$ is hydrogen, methyl, or ethyl;
$R_{11}$ is hydrogen, together with $R^9$ a double bond or together with $R^9$ an epoxy group —O—;
$R^{13}$ is hydrogen, methyl or ethyl;
$R^{15}$ is hydrogen, C$_1$-C$_4$-alkyl or, together with $R^{16}$, a —CH$_2$-group or a double bond;
$R^{16}$ is hydrogen or, together with $R^{15}$, a —CH$_2$-group or a double bond;

comprising:

a) reacting a compound of formula I

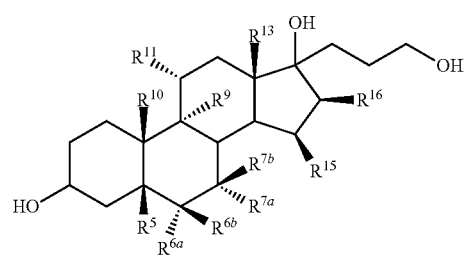

in which $R^5$ is hydroxy;

and $R^{6a}$, $R^{6b}$, $R^{7a}$, $R^{7b}$, $R^9$, $R^{10}$, $R^{11}$, $R^{13}$, $R^{15}$, $R^{16}$ have the same meaning as in formula III, with at least 3 molar equivalents of an organic or inorganic hypochlorite as an oxidizing agent in the presence of a catalytic amount of a 2,2,6,6-tetramethylpiperidine-N-oxide derivative at a pH of at least 8.0, to form a compound of formula II:

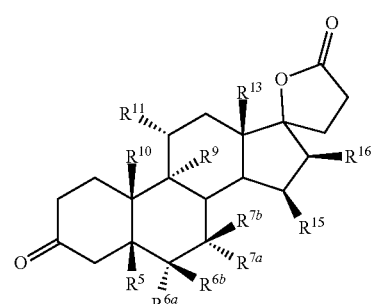

and b) subsequently converting the compound of formula II to a compound of formula III.

2. The process of claim 1, wherein said subsequent converting is conducted by eliminating water.

3. The process of claim 1, wherein the compound of formula II is isolated.

4. A process for the production of a 3-oxo-pregn-4-ene-21, 17-carbolactone of formula IIIa:

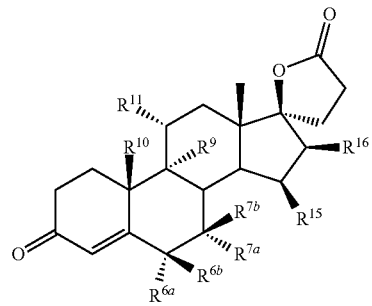

in which
- $R^{6a}$ is hydrogen or together with $R^{7a}$ a —CH$_2$ group;
- $R^{6b}$ is hydrogen or together with $R^{7b}$ a —CH$_2$-group;
- $R^{7a}$ is hydrogen, $C_1$—$C_4$-alkoxycarbonyl or $C_1$—$C_4$-thioacyl;
- $R^{7b}$ is hydrogen or together with $R^{6b}$ a —CH$_2$-group;
- $R^9$ is hydrogen, together with $R^{11}$ a double bond, or together with $R^{11}$ an epoxy group —O—;
- $R^{10}$ is hydrogen or methyl;
- $R^{11}$ is hydrogen, together with $R^9$ a double bond or together with $R^9$ an epoxy group —O—;
- $R^{15}$ is hydrogen or, together with $R^{16}$, a —CH$_2$-group or a double bond;
- $R^{16}$ is hydrogen or, together with $R^{15}$, a —CH$_2$-group or a double bond;

comprising:

a) reacting a compound of formula Ia:

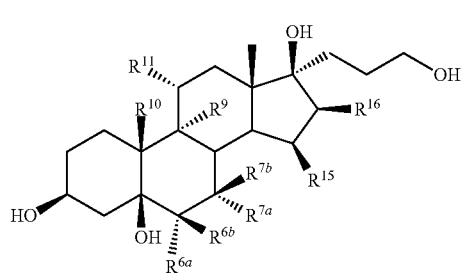

in which
$R^{6a}$, $R^{6b}$, $R^{7a}$, $R^{7b}$, $R^9$, $R^{10}$, $R^{11}$, $R^{15}$, $R^{16}$ have the same meaning as in formula IIIa, with at least 3 molar equivalents of an organic or inorganic hypochlorite as an oxidizing agent in the presence of a catalytic amount of a 2,2,6,6-tetramethylpiperidine-N-oxide derivative at a pH of at least 8.0, to form a compound of formula IIa:

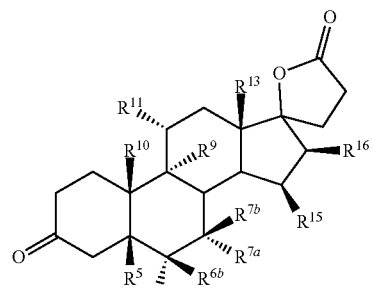

and b) subsequently converting the compound of formula IIa to a compound of formula IIIa.

5. The process of claim 4, wherein said subsequent converting is conducted by eliminating water.

6. The process of claim 4, wherein the compound of formula II is isolated.

7. A process for the production of a 3-oxo-pregn-4-ene-21, 17-carbolactone of formula IIIb:

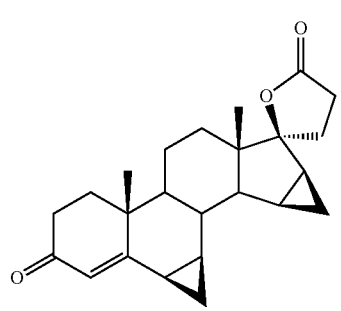

comprising:

a) reacting a compound of formula Ib:

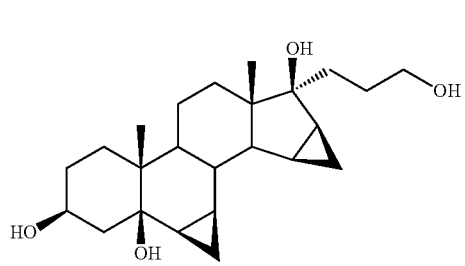

with at least 3 molar equivalents of an organic or inorganic hypochlorite as an oxidizing agent in the presence of a catalytic amount of a 2,2,6,6-tetramethylpiperidine-N-oxide derivative at a pH of at least 8.0, to form a compound of formula IIb:

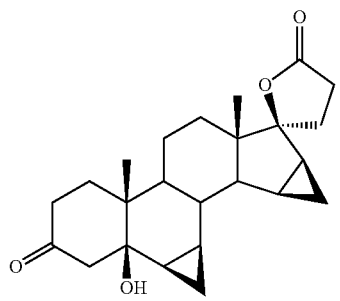

and
b) subsequently converting the compound of formula IIb to a compound of formula IIIb.

8. The process of claim 7, wherein said subsequent converting is conducted by eliminating water.

9. The process of claim 7, wherein the compound of formula II is isolated.

10. The process according to claim 1, wherein the reaction a) is performed in a two-phase solvent-water mixture.

11. The process according to claim 7, wherein the reaction a) is performed in a two phase solvent-water mixture.

12. The process according to claim 10, wherein the solvent is dichloromethane.

13. The process according to claim 11, wherein the solvent is dichloromethane.

14. A process according to claim 13, wherein the dichloromethane hemisolvate IV:

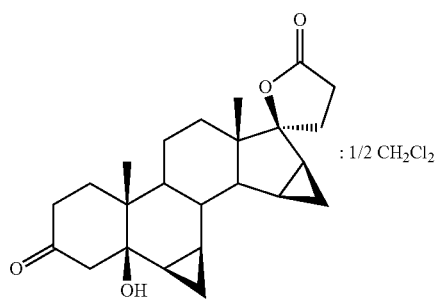

is produced from formula IIb before converting to formula IIIb.

15. The process according to claim 1, wherein 1-5 mol% of the 2,2,6,6-tetramethylpiperidine-N-oxide derivative is used.

16. The process according to claim 7, wherein 1-5 mol% of the 2,2,6,6-tetramethylpiperidine-N-oxide derivative is used.

17. The process according to claim 1, wherein 1-1.5 mol% of 2,2,6,6-tetramethylpiperidine-N-oxide is used.

18. The process according to claim 7, wherein 1-1.5 mol% of 2,2,6,6-tetramethylpiperidine-N-oxide is used.

19. The process according to claim 1, wherein 3-6 molar equivalents of alkali hypochlorite are used as the oxidizing agent.

20. The process according to claim 7, wherein 3-6 molar equivalents of alkali hypochlorite are used as the oxidizing agent.

21. The process according to claim 1, wherein 3-4 molar equivalents of sodium hypochlorite are used as the oxidizing agent.

22. The process according to claim 7, wherein 3-4 molar equivalents of sodium hypochlorite are used as the oxidizing agent.

23. The process according to claim 1, wherein the pH of the reaction in a) is between 8.5 and 10.0.

24. The process according to claim 7, wherein the pH of the reaction in a) is between 8.5 and 10.0.

25. The process according to claim 1, wherein the pH of the reaction in a) is set with potassium bicarbonate.

26. The process according to claim 7, wherein the pH of the reaction in a) is set with potassium bicarbonate.

27. The process according to claim 1, wherein the reaction temperature in a) is 0 to 20° C.

28. The process according to claim 7, wherein the reaction temperature in a) is 0 to 20° C.

29. The process according to claim 1, wherein, after the oxidation reaction is completed, a reducing agent for annihilating excess hypochlorite reagent is added to the reaction mixture.

30. The process according to claim 7, wherein, after the oxidation reaction is completed, a reducing agent for annihilating excess hypochlorite reagent is added to the reaction mixture.

31. The process according to claim 29, wherein the reducing agent is added with the addition of a base or a basic buffer at a pH of more than 5.

32. The process according to claim 30, wherein the reducing agent is added with the addition of a base or a basic buffer at a pH of more than 5.

33. The process according to claim 29, wherein an aqueous alkali hydrogen sulfite solution is used as the reducing agent.

34. The process according to claim 30, wherein an aqueous alkali hydrogen sulfite solution is used as the reducing agent.

35. The process according to claim 29, wherein, as the reducing agent, sodium hydrogen sulfite or potassium hydrogen sulfite is used in the form of the aqueous solution of sodium disulfite or potassium disulfite.

36. The process according to claim 30, wherein, as the reducing agent, sodium hydrogen sulfite or potassium hydrogen sulfite is used in the form of the aqueous solution of sodium disulfite or potassium disulfite.

37. The process according to claim 31, wherein sodium phosphate ($Na_3PO_4$) is used as a base or a basic buffer.

38. The process according to claim 32, wherein sodium phosphate ($Na_3PO_4$) is used as a base or a basic buffer.

* * * * *

UNITED STATES PATENT AND TRADEMARK OFFICE
CERTIFICATE OF CORRECTION

PATENT NO.        : 8,658,788 B2
APPLICATION NO.   : 13/187672
DATED             : February 25, 2014
INVENTOR(S)       : Seilz et al.

It is certified that error appears in the above-identified patent and that said Letters Patent is hereby corrected as shown below:

In the Claims:

Column 15, line 62 reads "$R^{6a, R6b}, R^{7a}, R^{7b}, R^9, R^{10}, R^{11}, R^{15}, R^{16}$ have the same" should read -- $R^{6a}, R^{6b}, R^{7a}, R^{7b}, R^9, R^{10}, R^{11}, R^{15}, R^{16}$ have the same --

Signed and Sealed this
Twenty-ninth Day of July, 2014

Michelle K. Lee
*Deputy Director of the United States Patent and Trademark Office*